United States Patent [19]
O'Lenick, Jr.

[11] Patent Number: 5,919,743
[45] Date of Patent: Jul. 6, 1999

[54] GUERBET BRANCHED QUATERNARY COMPOUNDS IN PERSONAL CARE APPLICATIONS

[75] Inventor: Anthony J. O'Lenick, Jr., Dacula, Ga.

[73] Assignee: Petroferm Inc., Fernandina Beach, Fla.

[21] Appl. No.: 09/221,731

[22] Filed: Dec. 28, 1998

[51] Int. Cl.⁶ .............................. C11D 1/40; C11D 1/52; C11D 1/62
[52] U.S. Cl. .................. 510/123; 510/130; 510/502; 510/504; 510/433; 134/42
[58] Field of Search ...................................... 510/123, 433, 510/502, 504, 130, 158, 159; 424/70.1; 514/881; 134/42

[56] References Cited

U.S. PATENT DOCUMENTS

| | | | |
|---|---|---|---|
| 5,318,727 | 6/1994 | Ohtawa et al. | 252/547 |
| 5,488,121 | 1/1996 | O'Lenick | 554/167 |
| 5,661,118 | 8/1997 | Cauwet et al. | 510/126 |
| 5,665,267 | 9/1997 | Dowell et al. | 510/123 |
| 5,712,232 | 1/1998 | Moriyama et al. | 510/120 |

*Primary Examiner*—John R. Hardee

[57] ABSTRACT

The present invention deals with a process for conditioning hair and skin using a novel guerbet based quat compounds. These materials are useful in personal care applications, where mildness, skin feel and conditioning on hair are desired.

18 Claims, No Drawings

GUERBET BRANCHED QUATERNARY COMPOUNDS IN PERSONAL CARE APPLICATIONS

BACKGROUND OF THE INVENTION

1. Field of the Invention

The present invention deals with use of novel, surfactants, specifically quats, based upon highly branched guerbet acids. The term "quats" is a shorthand for quaternary compounds.

2. Description of the Art Practices

Guerbet alcohols have been known for many years. Over the years there have been a number of derivatives patented. These materials can be oxidized into acids, which are raw materials for the preparation of the specific complex esters of the present invention. They possess the critical regiospecific guerbet linkage which when placed into amidoamine compounds and quats derived therefrom result in unexpected improvements in both liquidity and oxidative stability.

U.S. Pat. No. 5,488,121 to O'Lenick, incorporated herein by reference, discloses di-guerbet esters based upon the reaction product of both a guerbet acid and a guerbet alcohol. The guerbet acids of that invention are raw materials used in the preparation of the compounds of the present invention.

1. Field of the Invention

The present invention deals with novel cationic surfactants based upon a highly branched guerbet acid. The introduction of the guerbet branch into the quats of the present invention results in improved conditioning in personal care formulations as well as improved odor stability in the formulation and improved liquidity of the aqueous quat per se.

2. Description of the Art Practices

Quats are known in the art. Variation of carbon chain lengths in amido quats has direct effect upon the surfactant properties of the quat. While quats based upon short chain fatty acids can be made, they are germicidal and irritating to the skin and eyes. They also lack conditioning effects on hair. The use of fatty acids having more that 12 carbon atoms to make quats result in quats which provide foam in aqueous systems, but have little or no conditioning effects. The selection of a oleyl quats gives some improved viscosity, but the compound undergoes a process of oxidative instability referred to as rancidity, producing low molecular weight aldehydes with malodor. The availability of a liquid, oxidatively stable quat that can be used in personal care systems has been elusive prior to the compounds of the present invention.

The recent availability of guerbet acids and their reaction to make quats results in the preparation liquid stable quats, having outstanding emulsifying properties and are very acceptable for use in personal care applications.

None of the prior quats possess the critical guerbet moiety. Molecules of the current invention have the guerbet group in the quat.

THE INVENTION

This invention relates to a process for conditioning hair and skin which comprises contacting the skin with an effective conditioning amount of a quat derived from guerbet acid and conform to the following structure;

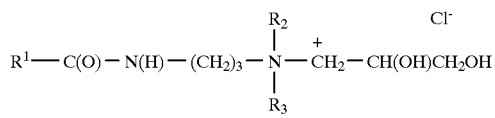

wherein:

$R^1$ is

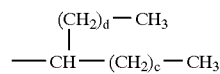

c and d are independently integers ranging from 3 to 17;

$R^2$ and $R^3$ are methyl or ethyl.

The presence of the —CH$_2$—CH(OH)CH$_2$OH functionality on the nitrogen results in improved water solubility, and also provides improved humectancy and conditioning effects to the quaternary compound.

The quat is prepared in a two step reaction. The first step is the preparation of a guerbet amidoamine conforming to the following structure:

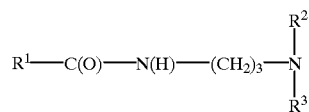

wherein:

$R^1$ is

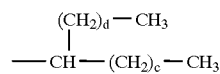

c and d are independently integers ranging from 3 to 17.

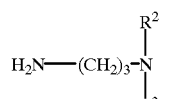

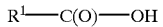

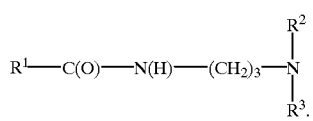

As previously stated another novel aspect of the present invention is the amidoamine intermediate conforming to the following structure:

$$R^1-C(O)-N(H)-(CH^2)_3-\underset{\underset{R^3}{|}}{\overset{\overset{R^2}{|}}{N}}$$

wherein:

$R^1$ is $$-CH-(CH_2)_c-CH_3 \atop \overset{|}{(CH_2)_d-CH_3}$$

c and d are independently integers ranging from 3 to 17.

In the second reaction the amidoamine, prepared in the first reaction, is reacted in aqueous solution with monochlorohydrin as follows:

$$R^1-C(O)-N(H)-(CH_2)_3-\underset{\underset{R^3}{|}}{\overset{\overset{R^2}{|}}{N}} +$$

$$Cl-CH_2CH(OH)CH_2OH \longrightarrow$$

(monochlorohydrin)

$$R^1-C(O)-N(H)-(CH_2)_3-\underset{\underset{R^3}{|}}{\overset{\overset{R^2}{|}}{\overset{+}{N}}}-CH_2CH(OH)CH_2OH$$

The concentration of the quat in water is generally between 20 and 50% with 35% being preferred. Glycols, lower alcohols and other polar solvents may also be added, if desired.

The quats of the present invention are formulated into personal care products for their superior conditioning effects, mild nature on skin and in the eyes and exceptional skin feel. The materials are applied to the hair or skin in aqueous solution or dispersion having between 0.1 and 50% by weight of the quat. The preferred concentration ranges from 10%–25% by weight.

Additionally, the compounds can be formulated with fatty alcohols, like cetyl alcohol (having 16 carbon atoms), stearyl alcohol (having 18 carbon atoms) or behenyl alcohol(having 22 carbon atoms). THe formulation so prepared will be referred to as a cream rinse and is applied to hair after washing with anionic surfactants, commonly sodium lauryl sulfate, or the like.

These quats have also been used in bath products and shower gels where their superior conditioning effects, mild nature on skin and in the eyes and exceptional skin feel. The materials are applied to the hair or skin in aqueous solution or dispersion having between 0.1 and 50% by weight of the quat. The preferred concentration ranges from 10%–25% by weight.

PREFERRED EMBODIMENTS

In a preferred embodiment said effective conditioning concentration ranges from between 0.1 and 50% by weight of the quat.

In another preferred embodiment said effective conditioning concentration ranges from between 10% and 25% by weight of the quat.

In a preferred embodiment c is 6, d is 3.
In another preferred emdobiment c is 7, d is 3.
In still another preferred embodiment c is 8, d is 4.
In another preferred emdodiment c is 9, d is 7.
In a preferred embodiment c is 16, d is 12.

EXAMPLES

RAW MATERIALS

Guerbet Acids $$CH_3-(CH_2)_{\bar{c}}-\underset{\underset{(CH_2)_d-CH_3}{|}}{CH}-C(O)-OH$$

(a Guerbet acid)

Vista Chemical practices the oxidation of guerbet alcohols commercially. The values of c and d were actually determined by analysis and are not dependant upon trade name for meaning.

| Example | Commercial Name | c | d |
|---|---|---|---|
| 1 | Isocarb 10 | 5 | 2 |
| 2 | Isocarb 12 | 6 | 2 |
| 3 | Isocarb 14 | 7 | 3 |
| 4 | Isocarb 16 | 8 | 4 |
| 5 | Isocarb 18 | 9 | 5 |
| 6 | Isocarb 20 | 9 | 7 |
| 7 | Isocarb 32 | 16 | 12 |
| 8 | Isocarb 40 | 19 | 15 |

Isocarb is a trademark of Vista.

Aminopropyl Amine

The compounds conform to the following structure:

Example 9

Dimethyl Aminopropyl Amine $$H_2N-(CH_2)_3-\underset{\underset{CH_3}{|}}{N}-CH_3$$

Example 10

Diethyl Aminopropyl Amine $$H_2N-(CH_2)_3-\underset{\underset{CH_2CH_3}{|}}{N}-CH_2CH_3$$

General Procedure

To the specified number of grams the specified dialkyl aminopropyl amine (Examples 9 and 10) is added the specified number of grams of the specified guerbet acid (examples 1–9) under agitation. The temperature of the mass is raised to 180–200 C and water is stripped off as formed. This temperature is held for between 1 and 12 hours. The acid value and the primary amine value drops to vanishingly small levels and the tertiary amine level approaches theoretical.

The products are clear liquids and are liquid to extraordinary temperatures.

| | Guerbet Acid | | Aminopropyl Amine | |
|---|---|---|---|---|
| Example | Example | Grams | Example | Grams |
| 11 | 1 | 171.0 | 9 | 122.0 |
| 12 | 2 | 199.0 | 9 | 122.0 |
| 13 | 3 | 227.0 | 9 | 122.0 |
| 14 | 4 | 255.0 | 9 | 122.0 |
| 15 | 5 | 283.0 | 9 | 122.0 |
| 16 | 6 | 311.0 | 9 | 122.0 |
| 17 | 7 | 479.0 | 9 | 122.0 |
| 18 | 8 | 592.0 | 9 | 122.0 |
| 19 | 1 | 171.0 | 10 | 150.0 |
| 20 | 2 | 199.0 | 10 | 150.0 |
| 21 | 3 | 227.0 | 10 | 150.0 |
| 22 | 4 | 255.0 | 10 | 150.0 |
| 23 | 5 | 283.0 | 10 | 150.0 |
| 24 | 6 | 311.0 | 10 | 150.0 |
| 25 | 7 | 479.0 | 10 | 150.0 |
| 26 | 8 | 592.0 | 10 | 150.0 |

The compounds are the intermediate conforming to the following structure:

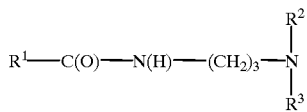

Monochlorohydrin is an item of commerce available from Phoenix Chemical in Somerville, N.J. and conforms to the following structure

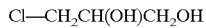

Quat Synthesis

To 120.0 grams of monochlorohydrin is added to the specified amount of water. The solution is heated to 80° C. and the amidoamine (examples 11–26) is added under agitation. The pH is kept between 8–9 by adding NaOH as required. The reaction progress is monitored by the inorganic chloride level, which within 3–4 hours reaches theoretical.

Example 27

To 120.0 grams of monochlorohydrin is added 1,000 grams of water. The solution is heated to 80° C. and 438.0 293.0 grams of amidoamine (example 27) is added under agitation. The pH is kept between 8–9 by adding NaOH as required. The reaction progress is monitored by the inorganic chloride level, which within 3–4 hours reaches theoretical.

Examples 28–42

Example 27 is repeated, only this time the specified amount and type of amido amine is substituted for the amido amine of example 27.

| | Amidoamine | |
|---|---|---|
| Example | Example | Grams |
| 28 | 12 | 321.0 |
| 29 | 13 | 349.0 |
| 30 | 14 | 377.0 |
| 31 | 15 | 405.0 |
| 32 | 16 | 433.0 |
| 33 | 17 | 601.0 |
| 34 | 18 | 714.0 |
| 35 | 19 | 320.0 |
| 36 | 20 | 351.0 |
| 37 | 21 | 399.0 |
| 38 | 22 | 407.0 |
| 39 | 23 | 435.0 |
| 40 | 24 | 470.0 |
| 41 | 25 | 631.0 |
| 42 | 26 | 743.0 |

The products produced using the examples 27–42 are clear yellow viscous liquids. The products have outstanding oxidative stability and provide conditioning when applied to the hair. In addition they are not irritating to the skin or eye.

What is claimed:

1. A process for conditioning hair or skin which comprises contacting the skin with an effective conditioning concentration of a guerbet quat which conforms to the following structure:

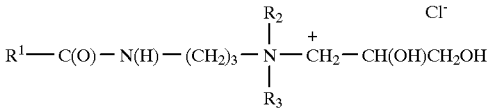

wherein:

$R^1$ is

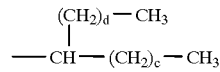

c and d are independently integers ranging from 3 to 17, $R^2$ and $R^3$ are methyl or ethyl.

2. A process of claim 1 wherein said effective conditioning concentration ranges from between 0.1 and 50% by weight of the quat.

3. A process of claim 1 wherein said effective conditioning concentration ranges from between 10% and 25% by weight of the quat.

4. A process of claim 1 wherein, c is 6, d is 3.
5. A process of claim 1 wherein c is 7, d is 3.
6. A process of claim 1 wherein c is 8, d is 4.
7. A process of claim 1 wherein c is 9, d is 7.
8. A process of claim 1 wherein c is 16, d is 12.
9. A process of claim 2 wherein, c is 6, d is 3.
10. A process of claim 2 wherein c is 7, d is 3.
11. A process of claim 2 wherein c is 8, d is 4.
12. A process of claim 2 wherein c is 9, d is 7.
13. A process of claim 2 wherein c is 16, d is 12.
14. A process of claim 3 wherein, c is 6, d is 3.
15. A process of claim 3 wherein c is 7, d is 3.
16. A process of claim 3 wherein c is 8, d is 4.
17. A process of claim 3 wherein c is 9, d is 7.
18. A process of claim 3 wherein c is 16, d is 12.

* * * * *